United States Patent
Mukkamala et al.

(10) Patent No.: US 10,251,566 B2
(45) Date of Patent: Apr. 9, 2019

(54) METHODS AND APPARATUS FOR DETERMINING A CENTRAL AORTIC PRESSURE WAVEFORM FROM A PERIPHERAL ARTERY PRESSURE WAVEFORM

(75) Inventors: Ramakrishna Mukkamala, Okemos, MI (US); Gokul Swamy, East Lansing, MI (US); Nicholas Bari Olivier, Haslett, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 2559 days.

(21) Appl. No.: 12/993,544

(22) PCT Filed: May 27, 2009

(86) PCT No.: PCT/US2009/045251
§ 371 (c)(1),
(2), (4) Date: Feb. 22, 2011

(87) PCT Pub. No.: WO2009/146312
PCT Pub. Date: Dec. 3, 2009

(65) Prior Publication Data
US 2011/0263989 A1    Oct. 27, 2011

Related U.S. Application Data

(60) Provisional application No. 61/128,956, filed on May 27, 2008.

(51) Int. Cl.
*A61B 5/021* (2006.01)
*A61B 5/029* (2006.01)

(52) U.S. Cl.
CPC .............. *A61B 5/021* (2013.01); *A61B 5/029* (2013.01); *A61B 5/02125* (2013.01)

(58) Field of Classification Search
CPC ... A61B 5/0059; A61B 5/0071; A61B 5/0084; A61B 5/02416; A61B 5/02154;
(Continued)

(56) References Cited

U.S. PATENT DOCUMENTS

| 4,429,701 A | 2/1984 | Goor et al. |
| 5,101,828 A | 4/1992 | Welkowitz et al. |

(Continued)

OTHER PUBLICATIONS

"Laguerre-Model Blind System Identification: Cardiovascular Dynamics Estimated From Multiple Peripheral Circulatory Signals" by McCombie et al., IEEE Transactions on Biomedical Engineering, vol. 52, No. 11, Nov. 2005.*

(Continued)

*Primary Examiner* — Tiffany Weston
(74) *Attorney, Agent, or Firm* — Harness, Dickey & Pierce, PLC

(57) ABSTRACT

A method is provided for determining a central aortic pressure (AP) wave-form for a subject. The method includes measuring a peripheral artery pressure (PAP) waveform from the subject, employing a distributed model to define a pressure-to-pressure transfer function relating PAP to AP and a pressure-to-flow transfer function relating PAP to a central arterial flow in terms of the same unknown parameters, estimating the unknown parameters by finding the pressure-to-flow transfer function, which when applied to the measured PAP waveform, minimizes the magnitude of the central arterial flow waveform during diastole, and applying the pressure-to-pressure transfer function with the estimated parameters to determine an AP waveform for the subject.

54 Claims, 4 Drawing Sheets

(58) Field of Classification Search
CPC ....... A61B 5/021; A61B 5/441; A61B 5/0205; A61B 5/0215; A61B 5/02152; A61B 5/02216; A61B 5/022; A61B 5/02208; A61B 5/02225; A61B 5/023; A61B 5/0235; A61B 5/02233; A61B 5/024; A61B 5/02438; A61B 5/026; A61B 5/028; A61B 5/0535; A61B 5/0452; A61B 5/4362; A61B 5/04011; A61B 5/0245; A61B 5/0464; A61B 5/222; A61B 5/0456; A61B 5/04004; A61B 5/044; A61B 5/029; A61B 5/1102; A61B 7/04; G01J 5/04; A61N 1/3702

USPC .......................................................... 600/485

See application file for complete search history.

(56) References Cited

U.S. PATENT DOCUMENTS

| | | | |
|---|---|---|---|
| 5,183,051 A | 2/1993 | Kraidin et al. | |
| 5,400,793 A | 3/1995 | Wesseling | |
| 5,423,322 A | 6/1995 | Clark et al. | |
| 5,437,285 A * | 8/1995 | Verrier et al. | 600/515 |
| 5,535,753 A | 7/1996 | Petrucelli et al. | |
| 6,368,284 B1 | 4/2002 | Bardy | |
| 6,428,482 B1 | 8/2002 | Sunagawa et al. | |
| 6,485,431 B1 | 11/2002 | Campbell | |
| 6,647,287 B1 | 11/2003 | Peel et al. | |
| 2003/0036685 A1* | 2/2003 | Goodman | 600/300 |
| 2003/0171682 A1 | 9/2003 | Zhang et al. | |

OTHER PUBLICATIONS

"Evaluation of the tracking potential of a noninvasive estimator of cardiac output" by Redling et al.*

"Non-invasive estimates of aortic root pressures: external subclavian arterial pulse tracing calibrated by oscillometrically determined brachial arterial pressures" by Aakhus et al., Clinical Physiology, vol. 13, pp. 573-586, 1993.*

"Systolic time intervals in clinical pharmacology" by Li et al., European Journal of Pharmacology, V. 44, pp. 415-421, 1993.*

Textbook of Medical physiology 11th edition by Guyton and Hall, p. 107, 2006.*

Aboy, et al., "Automatic Detection Algorithm for Physiologic Pressure Signal Components", *Proc. 2nd Joint EMBS/BMES Conference* (2002).

Antonelli, et al., "Wavelet Transform Analysis of the Arterial Pressure Signal", *Computers in Cardiology*, (1994).

Antonutto, et al., "Assessment of Cardiac Output from Noninvasive Determination of Arterial Pressure Profile in Subjects at Rest", *Eur. J. Appl. Physiol.* 69 (1994).

Appel, et al., "Beat-to-Beat Variability in Cardiovascular Variables: Noise or Music?", *J.Am. Coll. Cardiol.*, 14 (1989).

Bourgeois, et al., "Characteristics of Aortic Diatolic Pressure Decay with Application to Continuous Monitoring of Changes in Peripheral Resistance", *Circ. Res.*, 35 (1974).

Bourgeois, et al., "Continuous Determination of Beat-to-Beat Stroke Volume from Aortic Pressure Pulses in the Dog", *Circ. Res.*, 39(1) (1976).

Brubakk, A., "Use of Simulation Model for Estimating Cardiac Output from Aortic Pressure Curves", *Med & Biol. Eng. & Comput.*, 16 (1978).

Cerutti, et al., "Beat-to-Beat Stroke Volume Estimation from Aortic Pressure Signal in Conscious Rats: Comparison of Models", *Am J. Physiol.*, 281 (2001).

Cibulski, et al., "Pressure Methods for Estimating Right and Left Ventricular Stroke Volumes", *Am. J. Physiol.*, 225 (1973).

Connors, et al., "The Effectiveness of Right Heart Catheterization in the Initial Care of Critically Ill Patients", *JAMA*, 276 (1996).

Cundick, et al., "Clinical Comparison of Pressure-Pulse and Indicator-Dilution Cardiac Output Determination", *Circulation*, 62 (1980).

Ehlers, et al., "Cardiac Output Measurements. A Review of Current Techniques and Research", *Ann. Biomed. Eng.*, 14 (1986).

Fetics et al, "Parametric Model Derivation of Transfer Function for Noninvasive Estimation of Aortic Pressure by Radial Tonometry", IEEE Transactions on Biomedical Engineering, vol. 46, No. 6, Jun. 1999.

Fry, et al., "Measurement of Pulsatile Blood Flow by the Computer Pressure-Gradient Technique", *IRE Trans. Med. Electron., ME.* 6 (1959).

Fry, et al., "A Catheter Tip Method for Measurement of the Instantaneous Aortic Blood Velocity", *City Res.*, 4 (1956).

Gerhardt et al., "Non-Invasive Estimation of Cardiac Output in Critical Care Patients" *J. Clin. Monit.* 16 (2001).

Gratz, et al., "Continuous Noninvasive Cardiac Output as Estimated from the Pulse Contour Curve", *J. Clin. Monit.*, 8 (1992).

Greenfield, et al., "Relationship Between Instantaneous Aortic Flow and the Pressure Gradient", *Cir. Res.*, 17 (1965).

Guyton, A.C., "Testbook of Medical Physiology" W.B. Sanders Co., Philadelphia (1973).

Haffty, et al., "Noninvasive Tracking of Peripheral Resistance by Ear Densitography", *Chest* 83(5) (1983).

Hallock and Benson, "Studies on the Elastic Properties of Human Isolated Aorta", *Am. J. Physiol.*, 16 (1937).

Hamilton, et al., "The Measurement of the Stroke Volume from the Pressure Pulse", *Am. J. Physiol.*, 148 (14) (1947).

Harley, et al., "Pressure-Flow Studies in Man: Evaluation of the Duration of the Phases of Systole", *J. Clin. Invest.*, 48 (1969).

Herd, et al., "Arterial Pressure Pulse Contours During Hemmorrhage in Anesthetized Dogs", *J. Appl. Physiol.*, 21(6) (1966).

Houtman, et al., "Non-Invasive Cardiac Output Assessment During Moderate Exercise: Pulse Contour Compared with co2 Rebreathing", *Clin. Physiol.*, 19 (1999).

Imholz, et al., "Fifteen Years Experience With Finger Arterial Pressure Monitoring: Assessment of the Technology", *Cardiovasc. Res.*, 38 (19980.

Jin-Oh Hahn et al, "A new approach to reconstruction of central aortic blood pressure using adaptive transfer function", 20th Annual International IEEE EMBS Conference, Vancouver, British Columbia, Canada Aug. 20-24, 2008.

Jones, et al., "Velocity of Blood Flow and Stroke Volume Obtained from the Pressure Pulse", *J. Clin. Invest.*, 38 (1959).

Kenner, T., "Arterial Blood Pressure and its Measurement" *Basic Res. Cardiol.*, 83(2) (1988).

Kouchoukos, et al., "Estimation of Stroke Volume in the Dog by Pulse-Contour Method", *Cir. Res.*, 26 (1970).

Levett, et al., "Thermodilution Cardiac Output: A Critical Analysis and Review of the Literature", *J. Surg. Res.*, 27 (1979).

Ljung, L., "System Identification: Theory for the User" PTR Prentice Hall, Englewood Cliffs, N.J. (1987).

Linton, et al., "Estimation of Changes in Cardiac Output from the Arterial Blood Pressure Signal in the Upper Limb", *Br. J. Anaesth.*, 86 (2001).

MacDonald, "The Relation of Pulsatile Pressure to Flow in Arteries" *J. Physiol.* 127 (1955).

Martin et al., "Application of Pattern Recognition and Image Classification Techniques to Determine Continuous Cardiac Output from the Arterial Pressure Signal", *IEEE Trans. Biomed. Eng.*, 41 (1994).

McCombie, D. et al., "Multi-Channel Blind System Identification of the Arterial Network Using a Hemodynamic Wave Propagation Model", Proceedings of the 2004 American Control Conference, Boston, MA Jun. 30-Jul. 2, 2004.

McDonald, D.A., "Left Ventricular Output Derived from the Time-Derivative and Phase Velocities of the Aortic Pressure Wave", *Med. Biol. Eng.*, 11(6) (1973).

Navakatiyan, et al., "A Real-Time Algorithm for the Quantification of Blood Pressure Signals", *IEEE Trans. Biomed. Eng.*, 49(7) (2002).

Nichols, et al., "Continuous Cardiac Output Derived from the Aortic Pressure Signal: A Review of Current Methods", *Biomed. Eng.*, 8(9) (1973).

(56) References Cited

OTHER PUBLICATIONS

Osborn, et al., "The Measurement of Relative Stroke Volume from Aortic Pulse Contour Pulse Pressure", *Vasc. Dis.*, 5(3) (1968).
Perrott, et al., "An Efficient Approach to Arma Modeling of Biological Systems with Multiple Inputs and Delays", *IEEE Trans. Biomed. Eng.*, 43 (1) (1996).
Redling, et al., "Noninvasive Cardiac Output Estimation: A Preliminary Study", *Biol. Cybern.*, 77 (1997).
Remington, et al., "The Construction of a Theoretical Cardiac Ejection Curve from the Contour of the Aortic Pressure Pulse", *Am. J. Physiol.*, 144 (1945).
Robin, E.D., "Death by Pulmonary Artery Flow-Directed Catheter (Editorial). Time for a Moratorium?", *Chest*, 92(4) (1987).
Starmer, et al., "Evaluation of Several Methods for Computing Stroke Volume from Central Aortic Pressure", *Circ. Res.*, 33 (1973).
Starr, et al., "Studies Made by Simulating Systole at Necropsy. Iv. On the Relation Between Pulse Pressure and Cardiac Stroke Volume, Leading to a Clinical Method of Estimating Cardiac Output from Blood Pressure and Age", *Circulation*, 9 (1954).
Tajimi, et al., Evaluation of Pulse Contour Methods in Calculating Stroke Volume from Pulmonary Artery Pressure Curve (Comparison with Aortic Pressure Curve). *Eur. Heart J.*, 4 (1983).
Verdouw, et al., "Stroke Volume from Central Aortic Pressure? A Critical Assessment of the Various Formulae as to Their Clinical Value", *Basic Res. Cardiol.*, 70 (1975).
Warner, et al., "The Role of Computers in Medical Research", *JAMA*, 196 (1966).
Warner, et al., "Quantitation of Beat-to-Beat Changes in Stroke Volume from the Aortic Pulse Contour in Man", *J. Appl. Physiol.* 5 (1953).
Webster, J.G., "Measurement of Flow and Volume in Blood" in J.G. Webster, editor, "Medical Instrumentation. Application and Design" Houghton Mifflin, Bostin (1992).
Welkowitz, et al., "Noninvasive Estimation of Cardiac Output", *IEEE Trans. Biomed. Eng.*, 38(11) (1991).
Wellstead, et al., "Least-Squares Identification of Closed-Loop Systems", *Int. J. Control*, 21(4) (1975).
Womersley, J.R., "Method for the Calculation of Velocity, Rate of Flow and Viscous Drag in Arteries When the Pressure Gradient is Known", *J. Physiol.*, 127 (1955).
Wesseling et al., "Computation of Aortic Flow from Pressure in Humans Using a Nonlinear, Three-Element Model", *Am. J. Physiol.*, 74(5) (1993).
Wesseling et al., "A Simple Device for the Continuous Measurement of Cardiac Output. Its Model Basis and Experimental Verification" *Adv. Cardiovasc. Physc.* 5 (1983).
Gokul Swamy, Qi Ling, Tongtong Li, and Ramakrishna Mukkamala: "Blind identification of the aortic pressure waveform from multiple peripheral artery pressure waveforms", Am J Physiol Heart Circ Physiol, vol. 292, Jan. 5, 2007 (Jan. 5, 2007), pp. H2257-H2264, XP002540020.
Asada. H. H. et al: "Laguerre-Model Blind System Identification: Cardiovascular Dynamics Estimated From Multiple Peripheral Circulatory Signals", IEEE Transactions on Biomedical Engineering, IEEE Service Center, Piscataway, NJ, US, vol. 52, No. 11, Nov. 1, 2005 (Nov. 1, 2005) pp. 1889-1901, XP011140979, ISSN: 0018-9294.
Sugimachi Masaru et al: "A new model-based method of reconstructing central aortic pressure from peripheral arterial pressure", Japanese Journal of Physiology, Center for Academic Publications Japan, XX, vol. 51, No. 2, Apr. 1, 2002 (Apr. 1, 2001), pp. 217-222, XP002446121, ISSN: 0021-521X.
Stergiopulos N et al: "Physical Basis of Pressure Transfer From Periphery to Aorta: A Model-Based Study", American Journal of Physiology, American Physiological Society, Bethesda, MD, US, vol. 274, Apr. 1, 1998 (Apr. 1, 1998), pp. H1386-H1392, XP001035121, ISSN: 0002-9513.
Mark P. M. Harms, Karel H. Wesseling, Frank Pott, Morten Jenstrup, Jeroen Van Goudoever et al.: "Continuous stroke volume monitoring by modelling flow from non-invasive measurement of arterial pressure in humans under orthostatic stress", Clinical Science, vol. 97, 1999, pp. 291-301, XP002540019.
Nikos Stergiopulos, Berend E. Westerhof, Nico Westerhof: Total arterial inertance as the fourth element of the windkessel model:, Am J Physiol Heart Circ Physiol 276, vol. 276, 1999, pp. H81-H88, XP002540021.
International Preliminary Report on Patentability from corresponding PCT application, dated Dec. 9, 2010.

\* cited by examiner

METHODS AND APPARATUS FOR DETERMINING A CENTRAL AORTIC PRESSURE WAVEFORM FROM A PERIPHERAL ARTERY PRESSURE WAVEFORM

CROSS-REFERENCE TO RELATED APPLICATIONS

This application claims the benefit of U.S. Provisional Application No. 61/128,956, filed on May 27, 2008. The entire disclosure of the above application is incorporated herein by reference in its entirety.

GOVERNMENT RIGHTS

This invention was made with government support under 0643477 awarded by the National Science Foundation. The government has certain rights in the invention.

FIELD

The present disclosure relates to methods and apparatus for determining a central aortic pressure (AP) waveform from a single peripheral artery pressure (PAP) waveform via an adaptive transfer function.

BACKGROUND

As the arterial pressure wave traverses from the central aorta to the peripheral arteries, its contour becomes significantly distorted due to wave reflections in the arterial tree. Most notably, both systolic (maximum) pressure and pulse pressure (systolic minus diastolic (minimum) pressure) become amplified, with the extent of the amplification dependent on the circulatory state. Thus, it is the systolic and diastolic pressures measured specifically in the central aorta that truly reflect cardiac afterload and perfusion. Perhaps, as a result, central measurements of systolic pressure and pulse pressure have been shown to provide superior clinical information to corresponding measurements made in more peripheral arteries. Moreover, AP is less complicated by wave reflections than PAP. Thus, the entire AP waveform reveals each systolic ejection interval through the dicrotic notch (which is usually obscured in PAP waveforms) and often exhibits exponential diastolic decays with a time constant equal to the product of the total peripheral resistance and nearly constant arterial compliance (i.e., Windkessel time constant). The waveform may therefore be fitted to relatively simple, lumped parameter models (i.e., physical models not accounting for confounding wave reflections) in order to accurately estimate other clinically important cardiovascular variables such as relative cardiac output change and left ventricular ejection fraction. Methods and apparatus for effectively monitoring the AP waveform are therefore extremely desirable in that they would greatly facilitate the monitoring, diagnosis, and treatment of cardiovascular disease.

Conventionally, the AP waveform is measured by introduction of a catheter into a peripheral artery and placement of the catheter in the central aorta. However, this method is not commonly performed in clinical practice because of the risk of blood clot formation and embolization. On the other hand, PAP waveforms may be measured less invasively and more safely via placement of a catheter in a distal artery. Indeed, catheters are routinely placed in radial and femoral arteries in clinical practice. Moreover, over the past few decades, totally non-invasive methods have been developed and refined to continuously measure PAP based on finger-cuff photoplethysmography and applanation tonometry. These non-invasive methods are even available as commercial systems at present (see, for example, the Finometer and Portapres, Finapres Medical Systems, The Netherlands and the T-Line Blood Pressure Monitoring System, Tensys Medical Inc., San Diego, Calif.). In addition, non-invasive methods are commercially available and widely used for measuring signals closely related to PAP waveforms based on standard photoplethysmography.

A number of methods have previously been introduced to derive the AP waveform from related, but distorted, PAP waveforms. The most straightforward of the methods is to measure the PAP waveform at a superficial artery relatively close to the heart (e.g., the carotid artery) and simply use this measurement as a surrogate for the AP waveform. However, the AP and carotid artery pressure waveforms have been shown to be measurably different, especially during systole. But, an even greater drawback of this method is that the carotid artery is not commonly catheterized in clinical practice due to the high level of risk and is a technically difficult site to apply applanation tonometry due to surrounding loose tissue.

Several mathematical transformation methods have also been developed based on a generalized transfer function. These methods involve 1) initially obtaining simultaneous measurements of AP and PAP waveforms from a group of subjects, 2) estimating a group-averaged transfer function relating the measured PAP waveform to the measured AP waveform, and 3) subsequently applying this generalized transfer function to a PAP waveform measured from a new subject in order to predict the unobserved AP waveform. The principal assumption underlying these methods is that arterial tree properties are invariant over time and between individuals. However, the wealth of literature concerning the arterial tree indicates that this assumption is not nearly valid. For example, it is well known that arterial compliance varies with age and disease and that total peripheral resistance continually changes due to neurohumoral regulatory mechanisms. As a result, generalized transfer function methods can lead to significant discrepancies between estimated and measured AP waveforms as well as subsequently derived indices.

A method has recently been proposed towards adapting the transfer function relating PAP to AP to the inter-subject and temporal variability of the arterial tree. This method involves 1) using a tube model to define the transfer function in terms of physiologic parameters; 2) determining one of the parameters from an additional measurement and using population averages for the remaining parameters; and 3) applying the transfer function with these parameter values to the measured PAP waveform to predict the AP waveform. Since the degree of adaptation is only modest, this method was unable to show improved accuracy over the totally generalized transfer function methods.

Finally, a method has more recently been introduced to derive the AP waveform by identifying the commonality in multiple PAP waveforms using multi-channel blind system identification. While this method is able to fully adapt to the inter-subject and temporal variability of the arterial tree, only one PAP waveform is commonly measured in clinical practice.

It would be desirable to have a mathematical transformation for determining the AP waveform from a single PAP waveform that is able to completely adapt to the inter-subject and temporal variability of the arterial tree.

In this way, the AP waveform as well as other important cardiovascular variables could be accurately and conveniently monitored. Such a technique could, for example, be utilized for more effective hemodynamic monitoring in the intensive care unit, operating room, and recovery room in conjunction with an invasive PAP catheter already in place as well as in the emergency room, outpatient clinic, and at home in conjunction with a non-invasive PAP transducer.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A method is provided for determining an aortic pressure (AP) waveform for a subject. The method includes measuring a peripheral artery pressure (PAP) waveform from the subject, deriving a mathematical transformation relating PAP to AP using a distributed model and the criterion of negligible central aortic flow during diastole; and applying the derived mathematical transformation to the measured PAP waveform to determine the AP waveform for the subject.

The method for determining an aortic pressure (AP) waveform for a subject may also be characterized as follows. Measuring a peripheral artery pressure (PAP) waveform from the subject, employing a distributed model to define a pressure-to-pressure transfer function relating PAP to AP and a pressure-to-flow transfer function relating PAP to a central arterial flow in terms of the same unknown parameters, estimating the unknown parameters by finding the pressure-to-flow transfer function, which when applied to the measured PAP waveform, minimizes the magnitude of the central arterial flow waveform during diastole, and applying the pressure-to-pressure transfer function with the estimated parameters to determine an AP waveform for the subject.

Further areas of applicability of the present disclosure will become apparent from the detailed description provided hereinafter. It should be understood that the detailed description and specific examples are intended for purposes of illustration only and are not intended to limit the scope of the disclosure.

DRAWINGS

The present disclosure will become more fully understood from the detailed description and the accompanying drawings, wherein.

DETAILED DESCRIPTION

The present disclosure provides an improved means to mathematically derive an aortic pressure (AP) waveform from a single peripheral artery pressure (PAP) waveform. The key innovation is to fully adapt the mathematical transformation relating PAP to AP to the inter-subject and temporal variability of the arterial tree by using a distributed model in conjunction with the fact that central aortic flow is negligible during the diastolic intervals due to aortic valve closure (provided that aortic regurgitation is absent).

Figure 2:
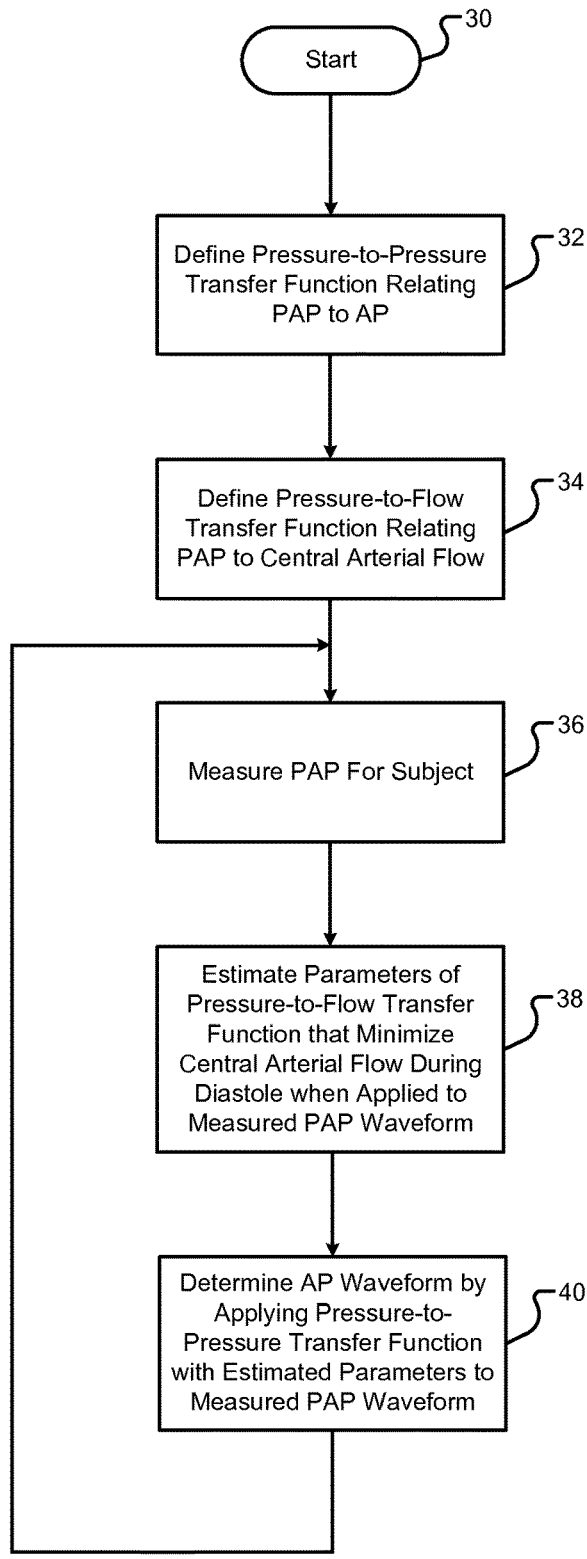
FIG. 2 is a flowchart depicting the general steps for deriving an aortic pressure waveform from a single PAP waveform.

FIG. 2 depicts the general steps for deriving an aortic pressure waveform from a single PAP waveform. First, a distributed model is employed to define the transfer function relating PAP to AP at step 32 and the transfer function relating PAP to a central arterial flow at step 34 in terms of the same unknown model parameters. A PAP waveform is measured at 36 from a subject. Next, the common parameters are estimated at 38 by finding the latter transfer function, which when applied to a measured PAP waveform segment, minimizes the magnitude of the central arterial flow waveform during diastole. The estimated parameters are then substituted into the former transfer function, and this transfer function is applied to the PAP waveform at 40 so as to derive the AP waveform. Note that the transfer function here is adaptive by virtue of updating its parameters each time a new PAP waveform segment becomes available for analysis. In addition, other cardiovascular variables may then be estimated from the derived AP waveform.

Detailed exemplary embodiments of the above general steps follow. This description is merely exemplary in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

In one exemplary embodiment, a PAP or related waveform is first measured from a subject and then digitized. The waveform may be obtained invasively or non-invasively using any of the methods known in the art of hemodynamic monitoring. However, it can be appreciated that other methods may be used to obtain the PAP waveform.

Second, the arterial tree is represented with a distributed model in order to define pressure-to-pressure and pressure-to-flow transfer functions with common parameters. In particular, referring now to FIG. 1A, the arterial tree 10 is modeled as a parallel arrangement of uniform tubes 14-1, 14-2, ..., 14-$m$ (collectively referred to as tubes 14) in series with lumped parameter terminal loads 16-1, 16-2, ..., 16-$m$ (collectively referred to as loads 16), respectively. The tube 14-$i$ (where i is an integer from 1 to m) represents the path between the aorta 12 and the peripheral artery. Each of the tubes 14 is frictionless and therefore has constant characteristic impedance ($Z_{ci}=\sqrt{(I_i/c_i)}$, where $I_i$ and $c_i$ are the tube's total inertance and compliance) and allows waves to propagate with constant velocity and delay time from one end of the tube to the other ($T_{di}$; $=\sqrt{(I_i c_i)}$). Thus, consistent with Poiseuille's law, mean pressure is identical throughout the tubes. The terminal load 16-$i$ signifies the arterial bed distal to the $i^{th}$ peripheral artery. Each terminal load has a frequency-dependent impedance ($Z_i(\omega)$, where $\omega$ is frequency) characterized by a single pole and single zero (at $-A_i$ and $-B_i$, where $0<A_i<B_i$) that may be dependent on the peripheral resistance and compliance as well as a gain factor equal to the characteristic impedance of the corresponding tube (i.e., $Z_{ci}$).

According to the arterial tree model, a PAP waveform $p_{pi}(t)$ is related to the AP waveform $p_a(t)$ through the pressure-to-pressure transfer function shown in FIG. 1B with unknown model parameters. Further, according to this model, the PAP waveform $p_{pi}(t)$ is related to a central arterial flow waveform $q_{ai}(t)$ (i.e., the arterial flow waveform at the tube entrance to the corresponding peripheral artery) through the pressure-to-flow transfer function shown in FIG. 10 with the same unknown model parameters as the pressure-to-pressure transfer function.

Third, the common unknown parameters of the transfer functions, namely $T_{di}$, $A_i$, and $B_i$, are estimated from each segment (e.g., every 15 sec interval) of the measured PAP waveform by exploiting the fact that central aortic flow is generally negligible during the diastolic intervals. Thus, as indicated in FIG. 1A, central arterial flow may likewise be small during these time intervals. In particular, the parameters are estimated by finding the pressure-to-flow transfer function, which when applied to the PAP waveform segment, minimizes the magnitude of the central arterial flow waveform (scaled by $Z_{ci}$) output over its diastolic intervals. In other words, as indicated in FIG. 1C, the parameters of the pressure-to-flow transfer function are determined so as to map the PAP waveform to a central arterial flow of zero during diastole.

To facilitate the parameter estimation, $T_{di}$, the wave propagation delay time between the central aorta and peripheral artery measurement site, may be measured first. A $T_{di}$ measurement is made for a subject during a monitoring period (e.g., on order of days), as arterial inertance and compliance may not greatly vary over this time period. Alternatively, periodic measurements may be made during a monitoring period. The $T_d$ measurement could be obtained non-invasively by, for example, applanating the carotid artery with a handheld tonometer and determining the time between the onsets of upstroke of the waveform that it measures and the peripheral ABP waveform. Other techniques for obtaining this measurement or an initial value for $T_{di}$ are also contemplated by this disclosure.

Then, all three parameters of the pressure-to-flow transfer function are estimated from each PAP waveform segment and the initial $T_{di}$ value as follows. Since the mean or DC value of $p_a(t)$ is already known (i.e., approximated as the corresponding value of $p_{pi}(t)$ or a slightly higher value due to Poiseuille's law), the DC value of $p_{pi}(t)$ is preferably removed in order to focus the mapping on the unknown zero-mean or AC components. Then, AC $q_{ai}(t)$ is calculated to within a $1/Z_{ci}$ scale factor by applying the pressure-to-flow transfer function to AC $p_{pi}(t)$ for candidate $A_i$ and $B_i$ values within the physiologic range and the initial $T_{di}$ value. The end of each diastolic interval of the candidate AC proportional $q_{ai}(t)$ is determined by identifying the minimum preceding the peak amplitude of a cardiac cycle, and the start of each corresponding diastolic interval is determined by identifying the minimum following the preceding peak amplitude of the cardiac cycle or approximated based on available formula relating the cardiac cycle length to the systolic interval length (e.g., Malik's or Bazett's formula). Then, the values of $A_i$ and $B_i$ are selected that provide the minimum variance (or any other magnitude metric known in the art of parameter estimation including the absolute value) of AC proportional $q_{ai}(t)$ over its diastolic intervals and preferably yield physiologically reasonable pressure and flow waveforms (e.g., AC proportional $q_{ai}(t)$ exhibits an undershoot during diastole as typically seen in experimental waveforms and $p_a(t)$, computed as described below, does not reveal double peaks). This optimization may be achieved using any available method known in the art of parameter estimation including a brute force numerical search over a physiologic range of $A_i$ and $B_i$ values or fast local search methods (e.g., simplex or Newton's method). Sub-optimal parameter values may also be selected. In the event that none of the $A_i$ and $B_i$ values in the search result in physiologically reasonable waveforms, $T_d$ is successively incremented when mean pressure decreases relative to the $T_{di}$ measurement period or decremented when mean pressure increases relative to this period (as $T_{di}$ tends to have an inverse relationship with mean pressure for significant changes) until the criterion is satisfied.

Next, the pressure-to-pressure transfer function, with the selected parameter values, is applied to $p_{pi}(t)$ (including its DC value or a slightly higher DC value) so as to derive $p_a(t)$. The derived waveform may be lowpass filtered (e.g., with a cutoff frequency of 10-20 Hz) to reduce any noise. The DC value of proportional $q_{ai}(t)$ may be determined by shifting the diastolic intervals of the AC waveform to zero amplitude. In this way, the relative change in a central arterial flow waveform may also be monitored.

Other embodiments of the above steps may also be employed. Some examples follow. The paths between the central aorta and peripheral arteries may be represented with non-uniform (e.g., tapered) tubes. The terminal loads may be represented with fewer parameters (e.g., a gain factor) or more parameters (e.g., a gain factor and multiple poles and zeros) to account for other peripheral phenomena (e.g., inertance). Alternatively, the terminal loads may be represented with an optimal number of parameters using various methods known in the art of parameter estimation. For example, for each PAP waveform segment for analysis, the parameter estimation may be carried out with a set of candidate loads characterized by a different number of poles and zeros, and the one that minimizes the magnitude of central arterial flow during diastole with a penalty factor for including additional parameters may then be selected.

In some embodiments, the parameter $T_{di}$ may be continuously approximated, rather than measured once or periodically, using other routine cardiovascular measurements. For example, $T_{di}$ may be estimated from the time interval between the R-wave of a surface ECG measurement and the onset of upstroke of the peripheral ABP waveform while accounting for the electromechanical delay and isovolumic contraction phase. Alternatively, $T_{di}$ may be approximated based on mean arterial pressure using various empirical formula known in the art of hemdoynamic monitoring. It is contemplated that the average or median of the estimated parameters over multiple segments of analysis may be used to reduce noise. In a less obvious example, the parameters may be estimated by minimizing the magnitude of central arterial flow during diastole and/or the fit between the average diastolic decay time constant of the AP waveform and the Windkessel time constant determined from the PAP waveform using another method. Further details regarding an exemplary method for determining the Windkessel time constant are found in U.S. Pub. No. 2004/0158163 A1.

The derived AP waveform may then be used to determine other clinically important cardiovascular parameters. For instance, parameters associated with AP may be identified from the waveform using any of the known blood pressure detection algorithms. Such parameters include systolic pressure, diastolic pressure, pulse pressure, and the systolic ejection interval. Other clinically important cardiovascular variables may also be estimated from the derived AP waveform using various known methods. One exemplary method fits a lumped parameter model to the derived waveform. Further details regarding this method are found in International Application No. PCT/US2007/006454 entitled "Method and Apparatus for Determining Ejection Fraction", which is incorporated herein by reference. Exemplary cardiovascular variables to be estimated include proportional total peripheral resistance, proportional cardiac output, proportional left ventricular end diastolic volume, proportional maximum left ventricular elastance, and absolute left ventricular ejection fraction.

The methods of the disclosure were tested using data collected from six dogs. Briefly, each dog was studied under general anesthesia as follows. A micromanometer-tipped catheter was placed in a femoral artery for the PAP waveform for analysis. A similar catheter was inserted into a peripheral artery and positioned in the ascending aorta for the reference AP waveform. The arterial pressure waveforms were then recorded during a baseline period and following of broad array of pharmacological, volume, and pacing interventions.

Figure 1:
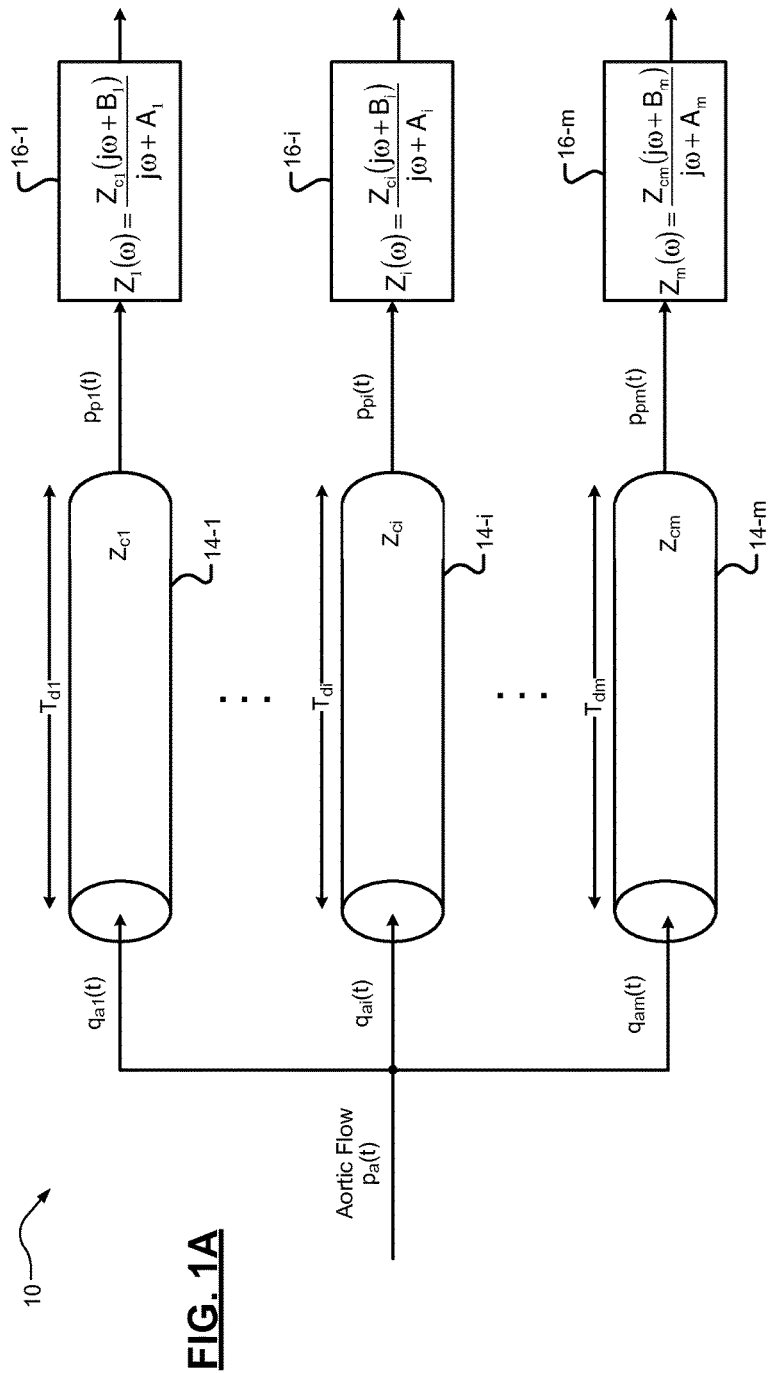
FIG. 1A is a schematic diagram of a tube model representing pressure and flow in the arterial tree according to the present disclosure.
FIG. 1B is a functional block diagram of a pressure-to-pressure transfer function according to the present disclosure.
FIG. 1C is a functional block diagram of a pressure-to-flow transfer function according to the present disclosure.

The methods of the disclosure, as embodied in FIG. 1 and now referred to as the adaptive transfer function (ATF) technique, were applied to the recorded PAP waveforms. The resulting derived AP waveforms were then quantitatively evaluated against the reference AP waveforms in terms of the sample-to-sample (total waveform, TW), beat-to-beat systolic pressure (SP), and beat-to-beat pulse pressure (PP) root-mean-squared-error (RMSE) values. The unprocessed PAP waveforms were likewise assessed with respect to the reference AP waveforms after time-aligning the two waveforms to eliminate error due merely to the wave propagation delay. For further comparison, AP waveforms were also derived by an autoregressive exogenous input-based generalized transfer function ($GTF_{ARX}$) technique (which was shown to be the most accurate amongst various generalized transfer function techniques) and the tube model-based partially adaptive transfer function ($PATF_{TUBE}$) technique (i.e., the transfer function shown in FIG. 1B with $T_{di}$ measured once for each dog and the same values for the $A_i$ and $B_i$ parameters for all dogs). The two previous transfer functions were established based on a subset of the canine data. The resulting derived AP waveforms were then likewise evaluated.

Figure 3:
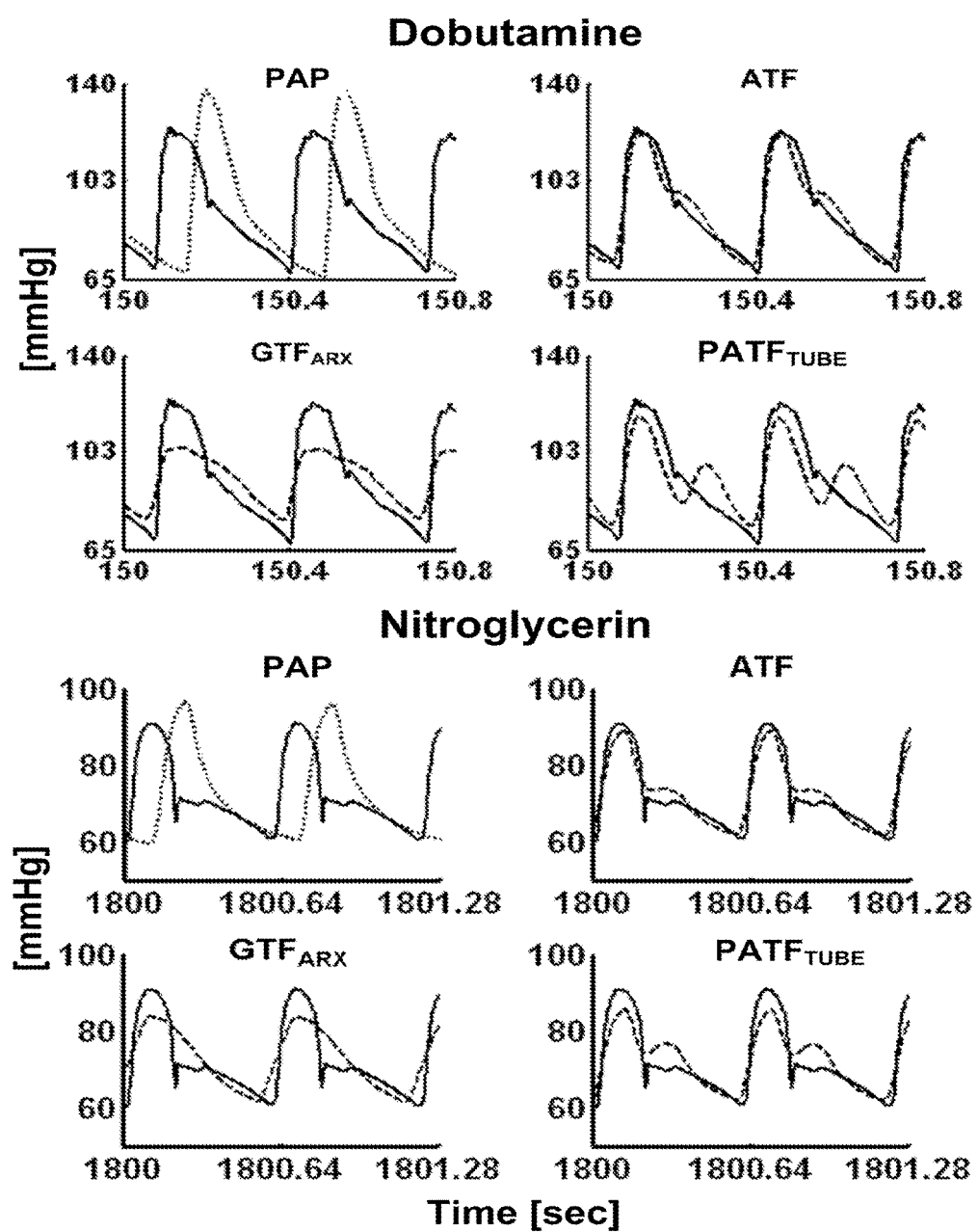
FIG. 3 are graphs illustrating measured AP and PAP waveforms and estimated AP waveforms during dobutamine and nitroglycerin conditions.

The Table below shows the TW, SP, and PP RMSE values of the PAP waveforms after time-alignment and the AP waveforms derived by the ATF technique as well as the previous $GTF_{ARX}$ and $PATF_{TUBE}$ techniques for each condition and overall. Referring now to FIG. 3, visual examples of the measured AP and PAP waveform segments and the corresponding derived AP waveform segments during the dobutamine and nitroglycerin conditions are illustrated. The results generally show that the AP waveforms derived by the ATF technique were in superior agreement to the reference AP waveforms than the unprocessed PAP waveforms and the AP waveforms derived by two previous transfer functions, which had the distinct advantage of being trained on a subset of the canine data.

TABLE

PAP and derived AP waveform errors.

| Condition | Time Aligned PAP | | | ATF | | | $GTF_{ARX}$ | | | $PATF_{TUBE}$ | | |
| --- | --- | --- | --- | --- | --- | --- | --- | --- | --- | --- | --- | --- |
| | TW | SP | PP | TW | SP | PP | TW | SP | PP | TW | SP | PP |
| | RMSE [mmHg] | | | RMSE [mmHg] | | | RMSE [mmHg] | | | RMSE [mmHg] | | |
| Baseline | 10.3 | 20.0 | 21.8 | 6.3 | 10.2 | 8.8 | 5.1 | 5.9 | 4.9 | 5.4 | 8.5 | 7.1 |
| Phenylephrine | 10.6 | 19.8 | 22.6 | 3.3 | 4.8 | 4.4 | 5.4 | 6.5 | 6.1 | 7.9 | 4.7 | 4.2 |
| Nitroglycerin | 3.1 | 1.9 | 2.0 | 3.8 | 6.9 | 6.6 | 5.3 | 9.4 | 8.2 | 4.4 | 8.0 | 7.8 |
| Dobutamine | 7.7 | 12.5 | 16.7 | 5.2 | 3.0 | 3.0 | 8.2 | 12.8 | 15.9 | 6.6 | 5.3 | 7.7 |
| Esmolol | 5.0 | 11.0 | 11.3 | 2.0 | 0.7 | 1.4 | 2.8 | 2.2 | 3.2 | 2.4 | 3.6 | 2.3 |
| Norepinephrine | 14.0 | 30.6 | 34.7 | 5.4 | 8.0 | 7.9 | 7.3 | 6.2 | 6.0 | 9.1 | 11.0 | 10.7 |
| Xylazine | 6.1 | 12.9 | 13.5 | 2.5 | 4.0 | 3.3 | 3.2 | 2.7 | 2.0 | 2.9 | 4.7 | 4.1 |
| Saline | 11.5 | 20.9 | 24.7 | 3.7 | 3.5 | 3.6 | 4.8 | 4.7 | 5.7 | 4.6 | 6.5 | 7.0 |
| Hemorrhage | 6.5 | 15.5 | 15.9 | 2.4 | 2.6 | 1.2 | 2.7 | 3.6 | 3.0 | 3.0 | 6.2 | 5.2 |
| Verapamil | 7.9 | 15.0 | 16.4 | 3.7 | 6.5 | 6.5 | 2.6 | 2.5 | 3.2 | 3.3 | 4.7 | 4.6 |
| High Rate Pacing | 7.6 | 13.3 | 21.2 | 4.0 | 2.7 | 4.3 | 2.6 | 2.6 | 4.7 | 3.8 | 6.0 | 6.5 |
| Vasopressin | 6.9 | 13.7 | 16.6 | 3.7 | 3.4 | 5.5 | 3.6 | 3.0 | 2.4 | 2.7 | 4.0 | 4.6 |
| Low Rate Pacing | 6.9 | 15.4 | 16.7 | 4.0 | 2.7 | 4.9 | 3.0 | 2.3 | 2.1 | 2.5 | 3.8 | 3.8 |
| Overall | 8.6 | 16.9 | 19.9 | 4.1 | 5.3 | 5.3 | 4.8 | 6.2 | 6.9 | 5.1 | 6.5 | 6.5 |

ATF is adaptive transfer function (invention); $GTF_{ARX}$, autoregressive exogenous input-based generalized transfer function; $PATF_{TUBE}$, tube model-based partially adaptive transfer function; TW, total waveform (i.e., sample-to-sample); and RMSE, root-mean-squared-error.

Figure 4:
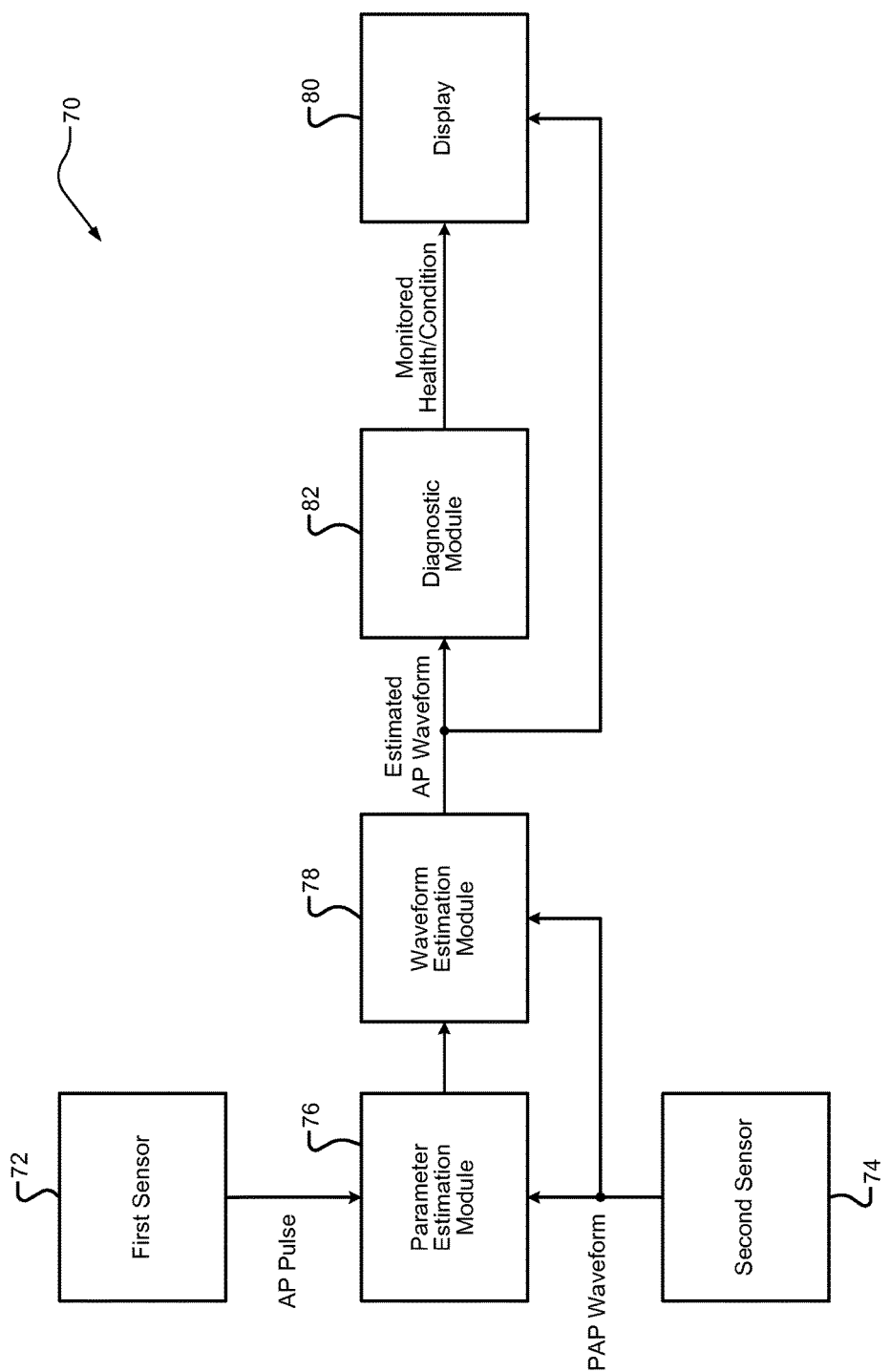
FIG. 4 is a functional block diagram of an apparatus implementing the methods according to the present disclosure.

Referring now to FIG. 4, an exemplary system 70 is shown that implements the methods according to the present disclosure. The system 70 includes a parameter estimation module 78 that estimates parameters of a transfer function relating PAP to AP according to the methods of the present disclosure. The system 70 may further include a first sensor 72, a second sensor 74, a waveform estimation module 78, a diagnostic module 82 and an output device such as a display 80. However, it can be appreciated that the system 70 may include fewer or additional modules and/or sensors.

The first sensor 72 is configured to detect an aortic pulse of the subject. The first sensor 72 detects the aortic pulse for purposes of determining the wave transmission delay time $T_{di}$ to a peripheral artery measurement site. In one embodiment, the first sensor 72 may detect an aortic pulse non-invasively from the carotid artery of the subject. For example, the first sensor 72 may be an applanation tonometer, but it can be appreciated that the first sensor 72 may be a different type of sensor. Additionally, it can be appreciated that the first sensor 72 may detect the aortic pulse using other methods and/or other arterial sites. In some embodiments, the first sensor 72 is not needed.

The second sensor 74 measures a PAP waveform or related waveform from the subject. In one embodiment, the second sensor 74 may measure the PAP waveform invasively from the femoral or radial artery of the subject. For example, the second sensor 74 may be a fluid-filled catheter, but it can be appreciated that the second sensor 74 may be a different type of sensor. Additionally, it can be appreciated that the second sensor 74 may measure the PAP waveform non-invasively and/or from other peripheral arteries.

The parameter estimation module 76 estimates parameters of a of a transfer function relating PAP to AP in the manner described above. In an exemplary embodiment, the parameter estimation module 76 receives the detected AP pulse from the first sensor 72 and the PAP waveform from the second sensor 74 and determines the wave transmission delay time $T_{di}$ of the subject. In one embodiment, the parameter estimation module 76 uses a timer to determine a delay between the detected AP pulse and a corresponding pulse in the PAP waveform. However, it can be appreciated that the parameter estimation module 76 may determine the wave transmission delay time $T_{di}$ using other methods and/or other signals from different sensors (a few of which have been described above).

Given the estimated parameters, the waveform estimation module 78 applies the pressure-to-pressure transfer function to a PAP waveform for the subject, thereby deriving an AP waveform for the subject. In an exemplary embodiment, the parameter estimation module 76 updates the parameters each time a new PAP waveform segment becomes available for analysis. In this case, the waveform estimation module 78 applies the transform function with the updated parameters to the same PAP waveform used to update the parameters. In another embodiment, parameters are updated less frequently such that the waveform segment module 78 applies the transform function to multiple PAP waveform segments for the subject without updating the parameters.

The diagnostic module 82 analyzes the AP waveform and determines a health condition of the subject and/or administers treatment to the subject based on the analysis of the AP waveform. The diagnostic module 82 receives the estimated AP waveform from the waveform estimation module 78. In one embodiment, the diagnostic module 82 monitors relative change in central arterial flow using the determined AP waveform. The diagnostic module 82 may also determine at least one parameter of the AP waveform. For example, the at least one parameter may include systolic pressure, diastolic pressure, pulse pressure, and systolic ejection interval.

The diagnostic module 82 may also estimate a cardiovascular variable from the AP waveform. For example, the diagnostic module 82 may estimate the cardiovascular variable from the estimated AP waveform using a lumped parameter model. The cardiovascular variable may be further defined as one of proportional cardiac output, proportional stroke volume, proportional total peripheral resistance, proportional maximum left ventricular elastance, and absolute left ventricular ejection fraction. In one embodiment, the diagnostic module 82 may calibrate the proportional cardiovascular variable to an absolute value using one of a nomogram, a single absolute measurement of cardiac output (e.g., thermodilution), and a single absolute measurement of ventricular volume (e.g., echocardiography). In one embodiment, an alarm is triggered upon excessive changes in any of the estimated variables. Lastly, the diagnostic module 82 may administer therapy to the subject, or modify the subject's therapy, based on one or more cardiovascular variables obtained according to the various methods presented herein.

The display 80 is configured to receive and display any of the derived waveforms and/or parameters noted above. For example, doctors and/or nurses may observe the estimated AP waveform to diagnose a condition of the subject or to monitor a condition of the subject. However, it can be appreciated that other types of output devices may be used in lieu of the display device.

The above description is merely exemplary in nature and is not intended to limit the present disclosure, application, or uses. As used herein, the term module refers to an Application Specific Integrated Circuit (ASIC), an electronic circuit, a processor (shared, dedicated, or group) and memory that execute one or more software or firmware programs, a combinational logic circuit, and/or other suitable components that provide the described functionality.

What is claimed is:

1. A method for determining a central aortic pressure (AP) waveform for a subject, comprising:
   measuring, by a sensor, a peripheral artery pressure (PAP) waveform from the subject;
   deriving a mathematical transformation relating PAP to AP using a distributed model, the transformation is defined in terms of unknown parameters;
   estimating, by a computing device, the unknown parameters by minimizing a variable representing a magnitude of central arterial flow during diastole when applied to the PAP waveform, wherein estimating the unknown parameters uses only one PAP waveform measured from the subject; and
   determining, by the computing device, the AP waveform for the subject by applying the derived mathematical transformation to the measured AP, where the steps of estimating and determining are implement by computer-executable instructions executed by a computer processor of the computing device.

2. The method of claim 1, wherein the distributed model includes one or more parallel tubes representing paths from a central aorta to a peripheral artery and corresponding lumped parameter terminal loads representing the arterial bed distal to the peripheral artery.

3. The method of claim 1 wherein deriving a mathematical transformation further comprises
   employing the distributed model to define a pressure-to-pressure transfer function relating PAP to AP in terms of unknown parameters and a pressure-to-flow transfer function relating PAP to a central arterial flow in terms of the same unknown parameters;
   estimating the unknown parameters by finding the pressure-to-flow transfer function, which when applied to the measured PAP waveform, minimizes the magnitude of the central arterial flow waveform during diastole.

4. The method of claim 3 wherein the unknown parameters are estimated to provide a minimum variance of the central arterial flow waveform during diastole.

5. The method of claim 3 wherein the unknown parameters are estimated to provide a minimum absolute value of the central arterial flow waveform during diastole.

6. The method of claim 3 wherein the unknown parameters are estimated with a numerical search over a physiologic range of parameter values.

7. The method of claim 3 wherein the unknown parameters are estimated with a local search method.

8. The method of claim 1 further comprises measuring another peripheral artery pressure (PAP) waveform from the subject and updating the unknown parameters using the another PAP waveform.

9. The method of claim 3 further comprises measuring another peripheral artery pressure (PAP) waveform from the subject and applying the derived mathematical transformation to the another PAP waveform.

10. The method of claim 1 further comprises measuring the PAP waveform invasively or non-invasively.

11. A method for determining a central aortic pressure (AP) waveform for a subject, comprising:
measuring, by a sensor, a peripheral artery pressure (PAP) waveform from the subject;
employing a distributed model to define a pressure-to-pressure transfer function relating PAP to AP and a pressure-to-flow transfer function relating PAP to a central arterial flow in terms of the same unknown parameters;
estimating, by a computing device, the unknown parameters by finding the pressure-to-flow transfer function, which when applied to the measured PAP waveform, minimizes a variable representing a magnitude of the central arterial flow waveform during diastole, wherein estimating the unknown parameters uses only one PAP waveform from the subject; and
applying, by the computing device, the pressure-to-pressure transfer function with the estimated parameters to determine an AP waveform for the subject, where the steps of estimating and determining are implemented by computer-executable instructions executed by a computer processor of the computing devices.

12. The method of claim 11, further comprising periodically repeating the steps of determining the AP waveform for the subject.

13. The method of claim 11, further comprising measuring the PAP waveform invasively or non-invasively.

14. The method of claim 13, further comprising measuring the PAP waveform with finger-cuff photoplethysmography or applanation tonometry.

15. The method of claim 11, wherein the distributed model includes one or more parallel tubes representing paths from the central aorta to a peripheral artery and corresponding lumped parameter terminal loads representing the arterial bed distal to the peripheral artery.

16. The method of claim 15, wherein the one or more parallel tubes are at least one of uniform, tapered, and frictionless.

17. The method of claim 15, wherein the corresponding lumped parameter terminal loads are characterized by a gain factor, a single pole, and a single zero.

18. The method of claim 15, wherein the corresponding lumped parameter loads are characterized by a gain factor.

19. The method of claim 15, wherein the corresponding lumped parameter loads are characterized by a gain factor, multiple poles, and multiple zeros.

20. The method of claim 11 wherein the unknown parameters include a wave transmission delay time.

21. The method of claim 20, further comprising measuring the wave transmission delay time non-invasively.

22. The method of claim 21, further comprising measuring the wave transmission delay time one time during a monitoring period of the subject.

23. The method of claim 22, further comprising measuring the wave transmission delay time by applanating a carotid artery and determining a time between an onset of upstroke of a waveform it measures and an onset of upstroke of the measured PAP waveform.

24. The method of claim 21, further comprising continuously approximating the wave transmission delay time using at least one additional measurement.

25. The method of claim 24, wherein the at least one additional measurement includes at least one of surface electrocardiogram and phonocardiogram signals.

26. The method of claim 21 wherein the measured wave transmission delay time is used as an initial value during the step of estimating the unknown parameters.

27. The method of claim 26, wherein values for the wave transmission delay time are derived from the initial value during the step of estimating the unknown parameters.

28. The method of claim 11, further comprising removing a mean value of the PAP waveform before estimating the unknown parameters.

29. The method of claim 11 further comprising calculating the central arterial flow waveform to within a scale factor.

30. The method of claim 29, further comprising identifying diastole from the central arterial flow waveform based on features of the central arterial flow waveform.

31. The method of claim 29, further comprising identifying diastole from the central arterial flow waveform based on features of the central arterial flow waveform and an empirical formula relating cardiac cycle length to systolic ejection interval.

32. The method of claim 31, wherein the empirical formula is Malik's formula or Bazett's formula.

33. The method of claim 11, wherein the unknown parameters are estimated to provide a minimum variance of the central arterial flow waveform during diastole.

34. The method of claim 11, wherein the unknown parameters are estimated to provide a minimum absolute value of the central arterial flow waveform during diastole.

35. The method of claim 11, further comprising the requirement that the parameter estimates yield physiologic pressure and flow waveforms.

36. The method of claim 35, wherein the physiologic waveforms are defined as one of central arterial flow waveforms with an undershoot during diastole and AP waveforms without double peaks.

37. The method of claim 11, wherein the unknown parameters are estimated with a numerical search over a physiologic range of parameter values.

38. The method of claim 11, wherein the unknown parameters are estimated with a local search method.

39. The method of claim 38, wherein the local search method is the simplex method or Newton's method.

40. The method of claim 11, further comprising determining an optimal number of parameters characterizing the distributed model.

41. The method of claim 40, further comprising estimating the unknown parameters for a set of candidate models characterized by a different number of parameters.

42. The method of claim 41, further comprising determining the model in the set of candidate models using criterion that penalize for inclusion of additional parameters.

43. The method of claim 11, further comprising estimating the unknown parameters by minimizing a fit between an average diastolic decay time constant of the AP waveform and a Windkessel time constant determined from the PAP waveform using another method.

44. The method of claim 11, further comprising low-pass filtering the determined AP waveform to reduce noise.

45. The method of claim 11, wherein a constant is added to the determined AP waveform.

46. The method of claim 45, wherein the constant is in a range from 1 to 3 mmHg.

47. The method of claim 11, further comprising monitoring relative change in central arterial flow.

48. The method of claim 11, further comprising determining at least one parameter of the AP waveform.

49. The method of claim 48, wherein the at least one parameter includes systolic pressure, diastolic pressure, pulse pressure, and systolic ejection interval.

50. The method of claim 11, further comprising estimating a cardiovascular variable from the derived AP waveform.

51. The method of claim 50, further comprising estimating the cardiovascular variable using a lumped parameter model.

52. The method of claim 50, wherein the cardiovascular variable is further defined as one of proportional cardiac output, proportional stroke volume, proportional total peripheral resistance, proportional maximum left ventricular elastance, and absolute left ventricular ejection fraction.

53. The method of claim 52, further comprising calibrating the proportional cardiovascular variable to an absolute value using one of a nomogram, a single absolute measurement of cardiac output, and a single absolute measurement of ventricular volume.

54. A system for determining a central aortic pressure (AP) waveform for a subject, comprising:

a sensor configured to obtain a peripheral artery pressure (PAP) waveform from the subject;

a parameter estimation module that estimates unknown parameters of a pressure-to-flow transfer function, from only one PAP wavefrom, by minimizing a variable representing central arterial flow during diastole when the pressure-to-flow transfer function is applied to the PAP waveform, where the pressure-to-flow transfer function relates PAP to a central arterial flow in terms of the unknown parameters; and a waveform estimation module that applies a pressure-to-pressure transfer function with the estimated parameters to the PAP waveform to determine an AP waveform for the subject, where the pressure-to-pressure transfer function relates PAP to AP in terms of the same unknown parameters, where the parameter estimation module and the waveform estimation module are implemented by computer-executable instructions executed by a computer processor of a computing device.

* * * * *